(12) United States Patent
Fahmy et al.

(10) Patent No.: US 11,457,943 B1
(45) Date of Patent: Oct. 4, 2022

(54) GRASPING PROSTATE MORCELLATOR

(71) Applicant: King Abdulaziz University, Jeddah (SA)

(72) Inventors: Usama Ahmed Fahmy, Jeddah (SA); Nabil Abdulhafiz Alhakamy, Jeddah (SA); Osama Abdulhakim Ali Ahmed, Jeddah (SA); Ashraf Bahi Eldin Abdel Naiem, Jeddah (SA); Basma Ghazi Eid, Jeddah (SA); Omar Ahmed Fahmy, Putrajaya (MY)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/505,843

(22) Filed: Oct. 20, 2021

(51) Int. Cl.
| | | |
|---|---|---|
| *A61B 17/30* | (2006.01) | |
| *A61B 17/32* | (2006.01) | |
| *A61B 90/00* | (2016.01) | |
| *G16H 40/63* | (2018.01) | |
| *G16H 20/40* | (2018.01) | |

(52) U.S. Cl.
CPC ........ *A61B 17/32002* (2013.01); *A61B 17/30* (2013.01); *A61B 90/361* (2016.02); *G16H 20/40* (2018.01); *G16H 40/63* (2018.01); *A61B 2017/320024* (2013.01); *A61B 2017/320064* (2013.01)

(58) Field of Classification Search
CPC ... A61B 17/32; A61B 17/32002; A61B 17/42; A61B 17/320016; A61B 2017/00544; A61B 2017/4216; A61F 9/00763
See application file for complete search history.

(56) References Cited

U.S. PATENT DOCUMENTS

| | | | | |
|---|---|---|---|---|
| 2,710,000 | A | * 6/1955 | Cromer | A61B 17/320016 600/568 |
| 5,688,234 | A | * 11/1997 | Frisbie | A61B 17/221 604/35 |
| 5,899,915 | A | 5/1999 | Saadat | |
| 2013/0090642 | A1 | 4/2013 | Shadduck et al. | |
| 2013/0123797 | A1 | 5/2013 | Livneh | |
| 2018/0085138 | A1 | 3/2018 | Preiss et al. | |

FOREIGN PATENT DOCUMENTS

| | | |
|---|---|---|
| CN | 106420009 A | 2/2017 |
| EP | 2 134 283 B1 | 6/2014 |

* cited by examiner

*Primary Examiner* — Vi X Nguyen
(74) *Attorney, Agent, or Firm* — Oblon, McClelland, Maier & Neustadt, L.L.P.

(57) ABSTRACT

A prostate grasping morcellator device and a method of morcellating prostate tissue are described. The prostate grasping morcellator device includes a handpiece portion including a motor which rotates an internal sheath in an external sheath of a rod. The rod is connected to a second end of the handpiece portion. The prostate grasping morcellator device includes one or more retractable grasping nails connected to an end of the rod. The end is distal to the second end of the handpiece portion. The prostate grasping morcellator device includes a control button to control movement of the retractable grasping nails. The control button is mounted adjacent to the second end of the handpiece portion. The prostate grasping morcellator device includes one or more blades, rotated by the motor to morcellate tissue.

7 Claims, 10 Drawing Sheets

GRASPING PROSTATE MORCELLATOR

STATEMENT OF ACKNOWLEDGEMENT

The inventors extend their appreciation to the Deputyship for Research and Innovation, Ministry of Education in Saudi Arabia for funding this research work through the project number 2021-013 and King Abdulaziz University, DSR, Jeddah, Saudi Arabia.

BACKGROUND

Technical Field

The present disclosure is directed to a prostate grasping morcellator device and a method of morcellating prostate tissue with the prostate grasping morcellator device.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Morcellation is division and cutting of large tissue masses into smaller pieces to allow them to be removed easily, e.g., removal from a body cavity as part of a surgical procedure. Morcellation is achieved using a surgical instrument known as a morcellator. Typically, the morcellator has sharp blade rotates that rotate at a tip or end of the morcellator with controlled speed to cut the tissue into small pieces which may then be suctioned through the morcellator to extract the tissue out of the morcellator and eventually outside the body. Traditionally, morcellators have been used to remove large sized organs located in abdominal cavity, such as the uterus or the kidney. The surgical procedure of the morcellation of prostate has been introduced recently after the introduction of endoscopic enucleation of very large prostate that is beyond the capability of endoscopic resection.

Morcellation of the prostate is challenging compared to abdominal organs due to limited working space and limited access inside the body. The abdominal cavity provides wide working space under clear vision and can typically be accessed from any part of surrounding skin without much limitation to size of the morcellator. However, for the prostate, the morcellation is performed inside the urinary bladder, by introducing the morcellator into the urinary bladder with aid of an endoscope through the urethra. In addition, vision is limited due to bleeding that occurs after enucleation of the prostate. Therefore, the surgical procedure demands a small size prostate morcellator (particularly a small diameter).

Further, in conventional procedures the tissue mass targeted for morcellation is held and maintained at the tip of a morcellator to be cut by a sharp blade. Some abdominal organ morcellators use a suction mechanism to hold the tissue at the tip of the morcellator. Due to the limitation of the diameter, the prostate tissue is held by creating a strong negative pressure at the tip of the morcellator to suck the tissue towards the morcellator tip. This carries the risk of sucking the bladder wall itself, which can cause significant bleeding and even bladder perforation with a significant morbidity risk for the patient. In addition, the prostate tissue tends to easily get loose and may drop from the morcellator tip when the negative pressure at the tip is interrupted during the morcellation. Such instances may prolong the surgical procedure because each time the tissue drops from the tip of the morcellator, the surgeon has to ensure that the bladder is fully distended and the prostate tissue is away from the bladder wall. Therefore, there is a need to provide reliable means to hold (or secure) tissues for such prostate morcellators while performing the prostate morcellation.

Various devices are known for performing such morcellation. For example, US2018/0085138A1 describes a device for selectively grasping and cutting tissue. The device includes an outer tube having a longitudinal axis, and an open proximal end and an open distal end. The device also includes a cup-shaped cutting member mounted to the distal end of the outer tube, where the cutting member is larger in diameter than a diameter of the outer tube. The device described in this reference grasps by moving an inner tube anteriorly and posteriorly inside an outer tube. The cutting mechanism is by a cup-shaped cutting member mounted to the distal end of the outer tube.

US5,899,915A describes apparatus and methods for intra-operatively performing surgery to create transmural channels in tissue using a device having a mechanical end effector and a stabilizing element in form of a suction cup for stabilizing the end effector in contact with the tissue. The device is for forming a tunnel inside tissues, not for removal of tissues or organs.

US2013/0090642A1 describes a surgical tissue cutting and extraction device including a sleeve having a tissue extraction lumen, with one or more jaw members coupled to the sleeve and configured to pivot or flex relative to the sleeve, to capture tissue. The device is for removal of portions of tissues only (such as fibroid lesion from uterus) but not effective for morcellation or removal of whole organs. It cannot be introduced to the bladder through a nephoscope. The device cuts tissue with heating using radiofrequency rather than mechanically.

EP2134283B1 describes a tissue removal device that may be used to remove uterine fibroids and other abnormal gynecological tissue. The tissue removal device includes an outer tube, an inner tube, and a motor assembly for rotating the inner tube relative to the outer tube and, at the same time, for translationally oscillating the inner tube relative to the outer tube. The tissue removal device also includes a grappling assembly with fingers to grab tissue, which may be retracted for the tissue to be severed. The device is for gynecological tissue and cannot be introduced to the bladder through a nephoscope. The tissue retraction mechanisms in this reference work through the inner tube.

CN106420009A describes a tissue morcellator cutter and laser therapy device. The tissue morcellator cutter includes a fixing seat and an outer sheath, where the outer sheath is a tubular structure, and one end of which is connected with the fixed seat. Metal wire at the distal end of this device is used to form a protective space between a knife and healthy tissue. The metal knife is not useful for grasping tissue.

US2013/0123797A1 describes a morcellator which may be operated with one hand, thus providing semi-automatic functionality, for the reduction of solid tissue into smaller pieces, which may then be transported and emptied into a specimen bag. The morcellator allows the surgeon to hold the scope and visualize the morcellation area. The device is for laparoscopic use in the intraabdominal cavity, not for endoscopic use or for prostate. The device cannot be introduced to the bladder through a nephroscope.

Each of the aforementioned references suffers from one or more drawbacks hindering their adoption. For example, US2018/0085138A1 provides the cup-shaped cutting member which may be unsuitable for prostate morcellation. US5,899,915A provides the stabilizing element in the form of the suction cup that stabilizes the cardiac tissue which may be unsuitable for prostate morcellation. US2013/0090642A1 provides the jaw members to capture tissue which may be unsuitable for prostate morcellation. EP2134283B1 provides the grappling assembly with the fingers to grab tissue which may be unsuitable for prostate morcellation. CN106420009A do not disclose means for trapping tissues, thereby rendering the tissue morcellator cutter and laser therapy device thereof unsuitable for prostate morcellation. US2013/0123797A1 do not disclose means for trapping tissues, thereby rendering the morcellator thereof unsuitable for prostate morcellation. Additionally, each of the aforementioned publications fails to disclose a morcellator device having a control button configured to control a movement of one or more retractable grasping nails, including retraction, in which the control button connects to a pair of wires on an external sheath with the pair of wires connecting to the retractable grasping nails.

Accordingly, it is one object of the present disclosure to provide a device and method for morcellating prostate tissue which has a suitable design (size) to allow for prostate morcellation and includes suitable means for grasping (trapping) tissues while performing the prostate morcellation.

SUMMARY

In an exemplary embodiment, a prostate grasping morcellator device is described. The prostate grasping morcellator device includes a handpiece portion having a motor connected to a power supply on a first end thereof. The motor rotates an internal sheath in an external sheath. The prostate grasping morcellator device also includes a rod connected to a second end of the handpiece portion and one or more retractable grasping nails connecting to an end of the rod that is distal to the second end of the handpiece portion. The prostate grasping morcellator device further includes a control button configured to control a movement of the one or more retractable grasping nails. The control button is mounted adjacent to the second end of the handpiece portion. The prostate grasping morcellator device further includes one or more blades rotated by the motor and configured to morcellate tissue. The prostate grasping morcellator device further includes a suction source configured to collect morcellated tissue pieces. The suction source is proximate to the first end of the handpiece portion.

In some embodiments, the control button controls retraction of the one or more retractable grasping nails. In some embodiments, the control button connects to a pair of wires on the external sheath. The pair of wires are connected to the retractable grasping nails. In some embodiments, the pair of wires are located inside a pair of tunnels. The pair of tunnels are in the external sheath.

In some embodiments, the one or more blades are adjacent to the one or more retractable grasping nails. In some embodiments, tips of the one or more blades are located distal to the second end of the handpiece portion. In some embodiments, the one or more retractable grasping nails are configured to trap tissue.

In some embodiments, the suction source connects to an opening. The opening is distal to the second end of the handpiece portion. The opening allows morcellated tissues to flow through the opening.

In another exemplary embodiment, a method of morcellating prostate tissue with a prostate grasping morcellator device is described. The method includes obtaining, by a camera, images of an environment surrounding tips of the prostate grasping morcellator device. The method further includes analyzing, by a processing circuitry, the images to obtain one or more parameters of the morcellator device. The method further includes morcellating, by the morcellator device, the prostate tissue based on the analysis. The prostate grasping morcellator device includes a handpiece portion having a motor connected to a power supply on a first end thereof. The motor rotates an internal sheath in an external sheath. The prostate grasping morcellator device further includes one or more retractable grasping nails connecting to an end of the rod that is distal to the second end of the handpiece portion. The prostate grasping morcellator device further includes a control button configured to control a movement of the one or more retractable grasping nails. The control button is mounted adjacent to the second end of the handpiece portion. The prostate grasping morcellator device further includes one or more blades rotated by the motor and configured to morcellate the prostate tissue. The prostate grasping morcellator device further includes a suction source configured to collect morcellated prostate tissue pieces. The suction source is proximate to the first end of the handpiece portion.

In some embodiments, the pair of wires are located inside a pair of tunnels. The pair of tunnels are in the external sheath. In some embodiments, the control button connects to a pair of wires on the external sheath. The pair of wires are connected to the retractable grasping nails. In some embodiments, the control button controls retraction of the one or more retractable grasping nails.

In some embodiments, the one or more blades are adjacent to the one or more retractable grasping nails. In some embodiments, the one or more retractable grasping nails are configured to trap tissue. In some embodiments, tips of the one or more blades are located distal to the second end of the handpiece portion.

In some embodiments, the suction source connects to an opening. The opening is distal to the second end of the handpiece portion. The opening allows morcellated prostate tissues to flow through the opening.

In another exemplary embodiment, a prostate grasping morcellator device is described. The prostate grasping morcellator device includes a handpiece portion having a motor and a control button. The prostate grasping morcellator device further includes a rod connecting to a first end of the handpiece portion. The prostate grasping morcellator device further includes a plurality of retractable grasping nails connected to an end of the rod. The prostate grasping morcellator device further includes a plurality of blades connected to the motor and the rod. The prostate grasping morcellator device further includes a suction source in fluid communication with the end of the rod adjacent to the plurality of blades.

In some embodiments, the motor rotates an internal sheath in an external sheath. In some embodiments, the end of the rod is distal to the handpiece portion. In some embodiments, the plurality of blades is used to morcellate the prostate tissues.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
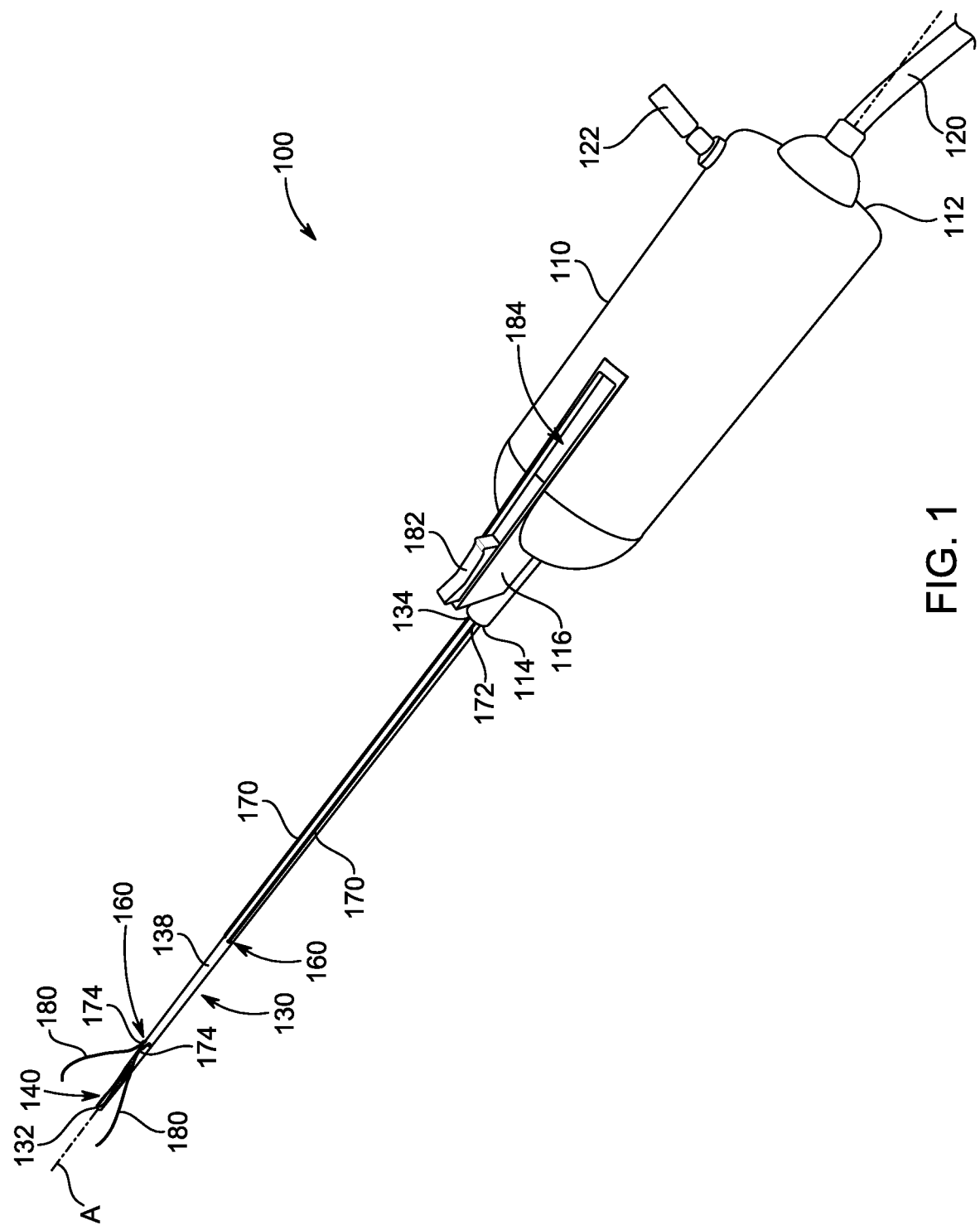
FIG. 1 is a perspective view of a prostate grasping morcellator device, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of the present disclosure are directed to a prostate grasping morcellator device which provides a mechanism for removing prostate tissues from urinary bladder, for example, after endoscopic enucleation using laser or plasma procedures. The prostate grasping morcellator device can grasp the prostatic tissues with aid of retractable grasping nails without need for a forceful suction (vacuum) to keep the prostate tissues in contact with blades therein. The configuration of the prostate grasping morcellator device allows morcellating the prostate tissue in a continuous manner.

Figure 2:
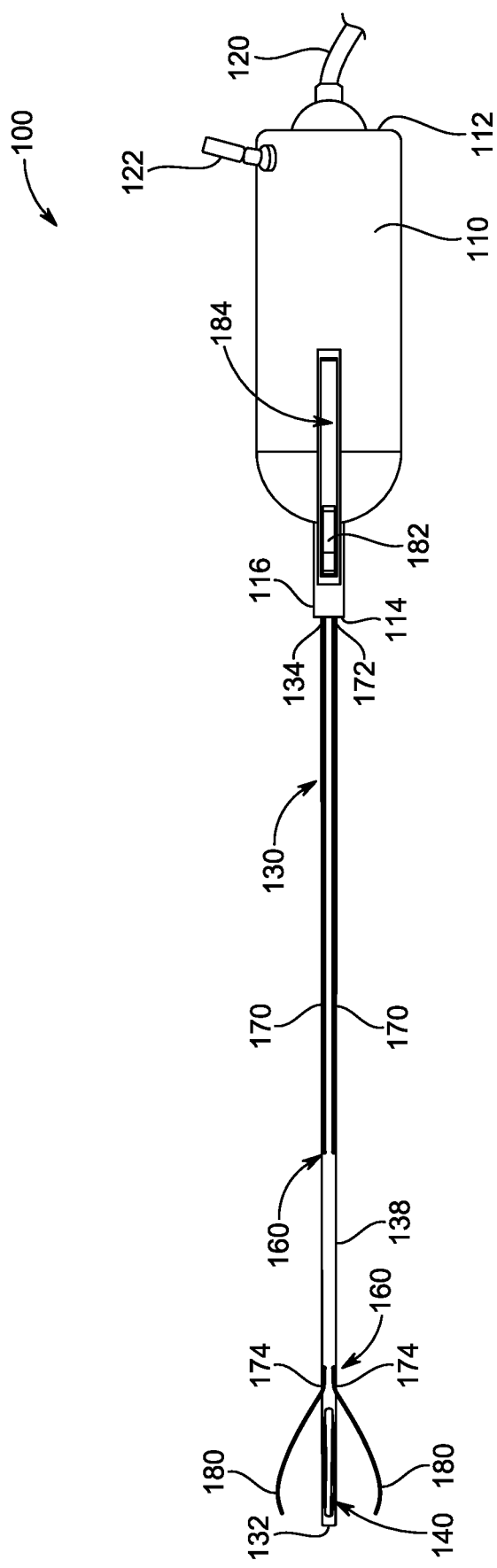
FIG. 2 is a top view of the prostate grasping morcellator device of FIG. 1, according to certain embodiments.

Referring to FIG. 1 and FIG. 2, a perspective view, and a top view of a prostate grasping morcellator device 100 is illustrated, respectively. In the present disclosure, the prostate grasping morcellator device 100 (hereinafter referred to as "the morcellator device 100") is generally described for the purposes of morcellating prostrate tissue, such as removing prostate lobes from the urinary bladder after endoscopic enucleation using laser or plasma procedures. However, it is contemplated that the morcellator device 100 may be implemented and/or adapted to be used for morcellation of other types of tissues including, but not limited to, abdominal tissue inside abdominal cavity, such as uterus or kidney, gynecological tissue, cardiac tissue, and the like. In general, the term "morcellator device" is used herein to cover any surgical instrument used for division and removal of large masses of tissues during surgery, in which an organ or a portion of an organ is minced up, or morcellated, into smaller pieces inside the patient's body for subsequent extraction from the patient's body.

The morcellator device 100 includes a handpiece portion 110. The term "handpiece portion" is intended to broadly refer to part(s) of the morcellator device 100 that is held/gripped by a user (such as, a surgeon during surgical operation). The handpiece portion 110 may generally be hollow to accommodate various components that aid operation of the morcellator device 100. The handpiece portion 110 may have a one-part housing, or a housing configured to accommodate two or more parts that may be physically integrated with one another or spatially separated from one another. The handpiece portion 110 defines a first end 112 and a second end 114 along a longitudinal axis "A" of the morcellator device 100. In an example, as illustrated, the handpiece portion 110 may generally be cylindrical in shape. Further, the handpiece portion 110 includes an extended member 116 extending in a direction towards the second end 114 of the handpiece portion 110. It should be appreciated that the illustrated shape and design for the handpiece portion 110 is exemplary in nature and should not be construed as limiting. In some embodiments, the handpiece portion 110 may have any other suitable shape, such as cuboidal or the like, and/or may exclude the extended portion 116.

The extending member 116, along with a main body of the handpiece portion 110, defines a groove 184 extending along the longitudinal axis "A" of the morcellator device 100, as illustrated. A control button 182 (also referred to as "the first control button 182") is operably disposed in the groove 184, such that a portion of the control button 182 extends from a surface of the groove 184 to allow access to the control button 182. In a default position, the control button 182 is disposed proximal to the second end 114 of the handpiece portion 110. As used herein, the term "operably disposed" refers to a configuration of the control button 182 and the groove 184 that together allows the control button 182 to be slid along a length of the groove 184. The term "default position" refers to a rest position of the control button 182 prior to being accessed by the user, such as the surgeon, handling the morcellator device 100.

The handpiece portion 110, besides other components, houses a motor 802 (see FIG. 8), which is described later with reference to FIG. 8. A power supply 120, illustrated through a power cord, is coupled to the first end 112 of the handpiece portion 110. The term "power supply", as used herein, may include, for example, but not limited to, a battery, an AC/DC power supply, a renewable power source, a non-renewable power source, a generator, and the like. For example, in cases where the power supply 120 is the AC/DC power supply, a corresponding wire to receive electrical power from, for example, a power socket may be connected at the first end 112 of the handpiece portion 110. In other examples where the power supply 120 is the battery, the battery may be disposed within the handpiece portion 110. The handpiece portion 110 further includes a suction source 122 located proximal to the first end 112 of the handpiece portion 110. The suction source 122 may be, for example, a vacuum source external to the handpiece portion 110 and connected via a pipe or the like (as shown and generally represented as the suction source 122 in FIG. 1 and FIG. 2) to the first end 112 of the handpiece portion 110. In some embodiments, the suction source 122 may be configured to draw electrical power from the power supply 120 for its operation. The suction source 122 is configured to collect morcellated tissue pieces.

The morcellator device 100 further includes a rod 130 extending along the longitudinal axis "A" and connected to the second end 114 of the handpiece portion 110. Length of the rod 130 may be predefined based on an application of the morcellator device 100, such as morcellating prostate tissues, abdominal tissues, or the like. The rod 130 defines a first end 132 (active end) and a second end 134 (connecting end). The first end 132 of the rod 130 is distal to the second end 114 of the handpiece portion 110 and the second end 134 of the rod 130 is proximal, specifically attached, to the second end 114 of the handpiece portion 110. The first end 132 of the rod 130 may be understood as the operational (active) end of the rod 130, for the purposes of the present disclosure.

The morcellator device 100 further includes one or more retractable grasping nails 180, hereinafter individually and collectively referred to as "the grasping nail(s) 180", connected to a location proximal the first end 132 of the rod 130. As illustrated in FIG. 2, each grasping nail 180 is located on one end of the rod 130 corresponding to the default position of the control button 182.

Figure 3:
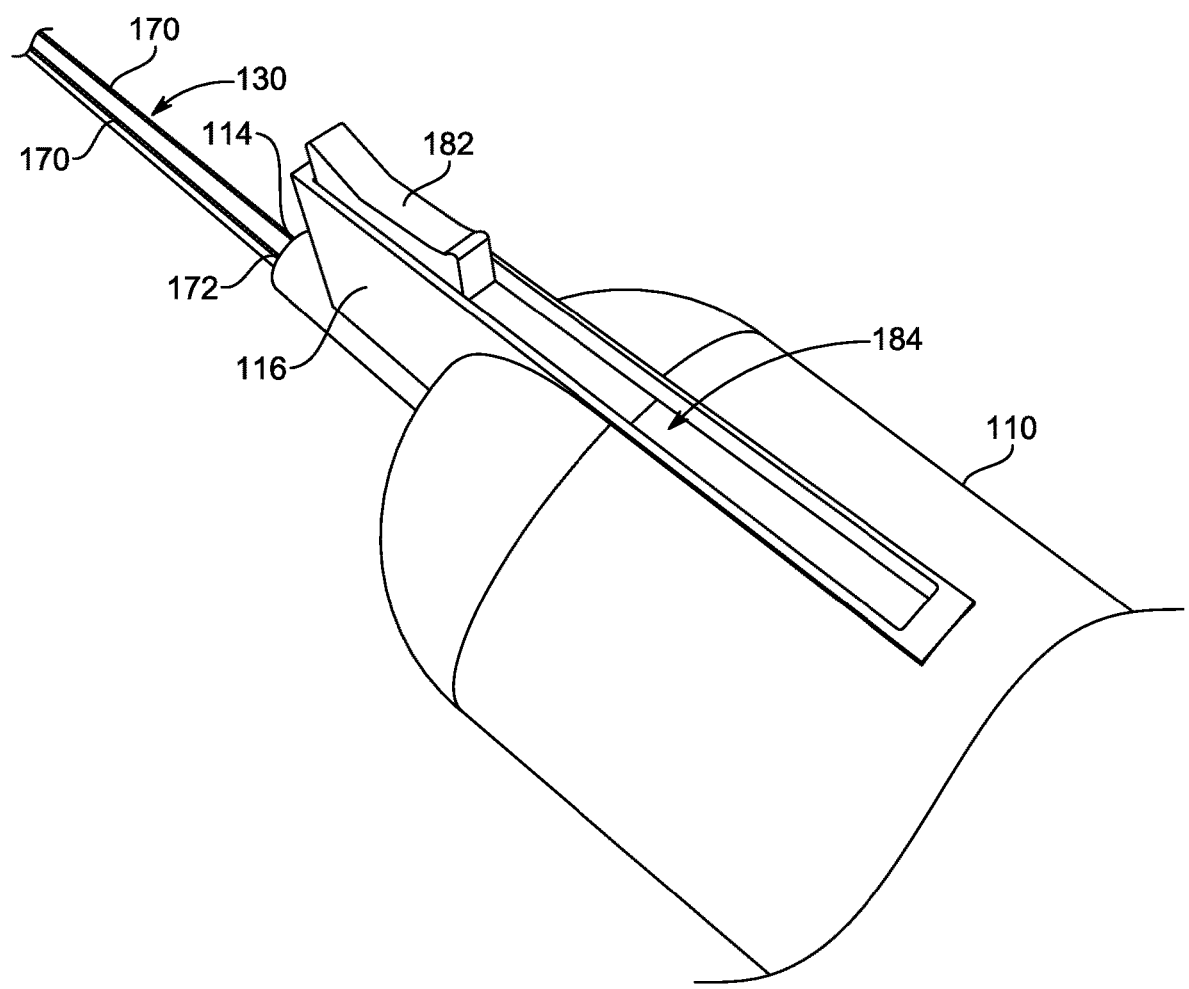
FIG. 3 is an enlarged perspective view of a portion of the prostate grasping morcellator device of FIG. 1 showing a groove within which a control button moves between a first position and a second position thereof, according to certain embodiments.

FIG. 3 illustrates an enlarged view of a portion of the morcellator device 100 of FIG. 1. The morcellator device 100 further includes a pair of wires 170, hereinafter individually and collectively referred to as "the wire(s) 170". As used herein, the term "wire" includes a single wire or multiple wires together constituting the wire 170, each of which is allowed for use in surgical instruments. A first end 172 of each wire 170 is coupled to the control button 182. For the purpose, the first end 172 of each wire 170 may be routed through the extending member 116 and connected to a base (not shown) of the control button 182. Length of each wire may be predetermined based on the length of the rod 130. In some embodiments, the morcellator device 100 may be configured to allow the user to change the wires 170 after each surgical procedure. As such, the control button 182 may be manually disengaged from the handpiece portion 100 for connecting the base thereof with the wires 170. Further, in some embodiments, a length of the groove 184 may correspond to the length of the wires 170.

Figure 4:
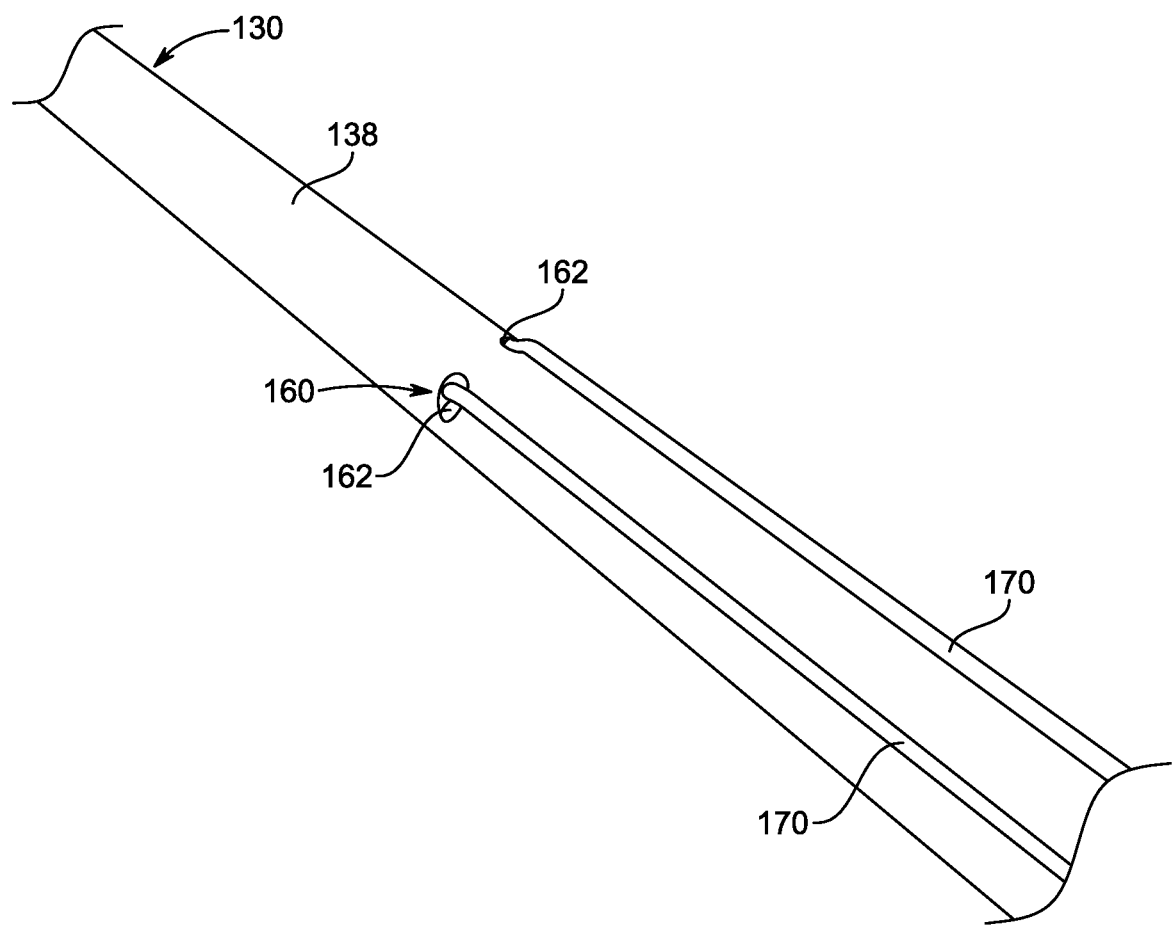
FIG. 4 is an enlarged perspective view of a portion of a rod of the prostate grasping morcellator device of FIG. 1, according to certain embodiments.
Figure 5:
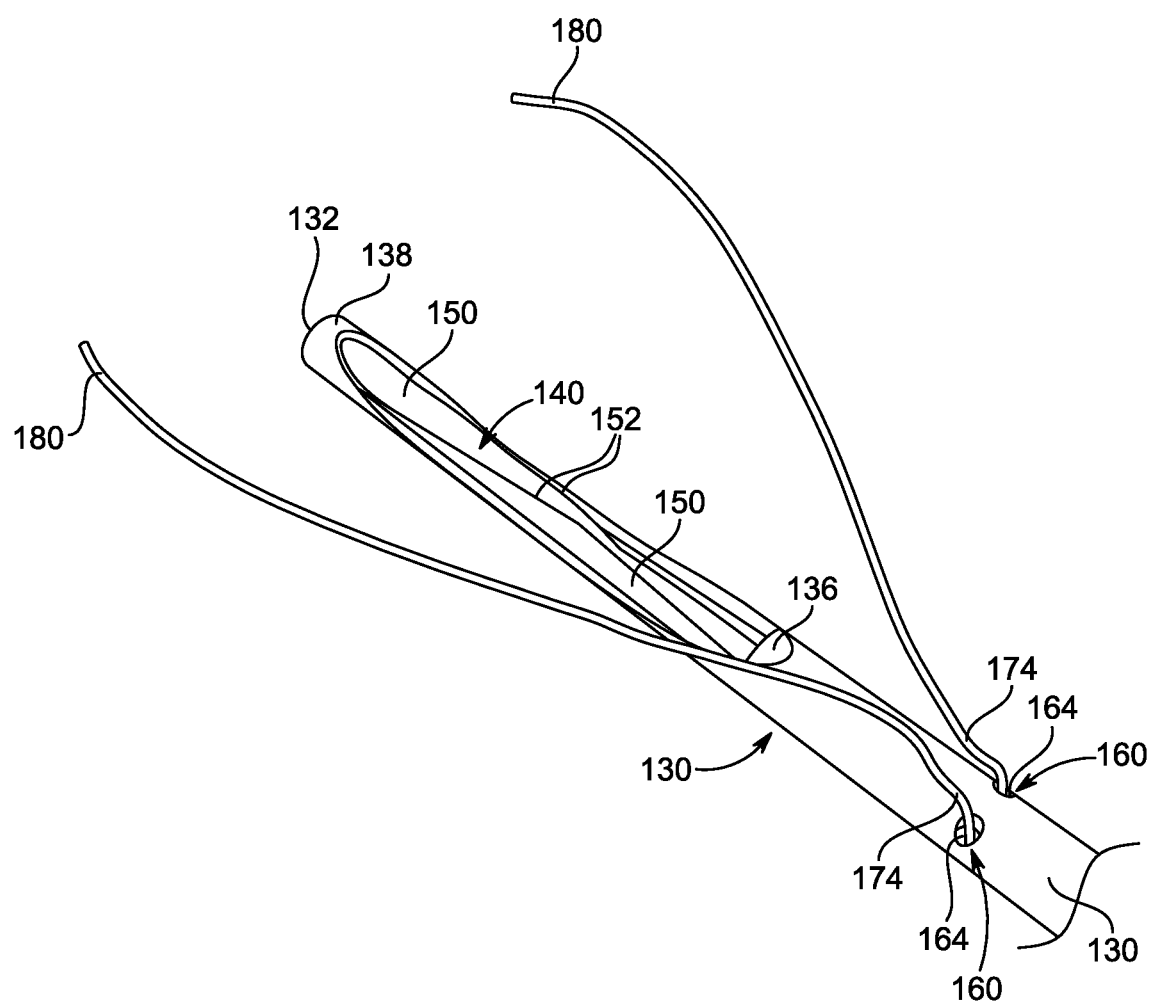
FIG. 5 is an enlarged perspective view of a another portion of the rod, according to certain embodiments.

Referring to FIG. 4, the rod 130 defines a pair of tunnels 160, opening of which are referenced with the numerals 162 and 164 (see FIG. 5). The openings 162 are located adjacent to each other on the rod 130 and proximal to the second end 114 of the handpiece portion 110. Each wire 170 extending from the second end 114 of the handpiece portion 110 is routed into one tunnel 160 through corresponding opening 162. Preferably, the wires 170 are routed parallel to each other along the longitudinal axis "A" of the morcellator device 100.

FIG. 5 illustrates an enlarged view of a portion of the rod 130. Particularly, FIG. 5 illustrates an enlarged view of the operational end of the rod 130. A second end 174 of each wire 170 is routed out of the corresponding tunnel 160 through respective opposite opening 164. The term "opposite", as used herein, refers to another end of the tunnel 160 with respect to the opening 162. The rod 130 includes an internal sheath 136 and an external sheath 138 (also shown in FIG. 4), where the external sheath 138 defines an outer surface of the rod 130. The internal sheath 136 and the external sheath 138 may be embodied as sleeves, and the internal sheath 136 is disposed coaxially within the external sheath 138. In such configuration, the rod 130 may have a radial gap (not shown) defined between the internal sheath 136 and the external sheath 138, to allow a relative movement of the internal sheath 136 with respect to the external sheath 138 along the longitudinal axis 'A' and about the longitudinal axis "A".

The rod 130 defines an opening 140 extending along the longitudinal axis "A" and located distal with respect to the second end 114 of the handpiece portion 110. In particular, the opening 140 is located proximal to the first end 132 of the rod 130 and extends along a portion of the rod 130. The opening 140 is generally in the form of a rectangular cut-out defined along portions of circumferential walls of the internal sheath 136 and the external sheath 138, such that an internal portion of the rod 130 is visible to the user. In an embodiment, the suction source 122 is connected to, for example, in fluid communication with, the opening 140 via the handpiece portion 110 and the rod 130.

The morcellator device 100 further includes one or more blades 150 coupled to the internal sheath 136. The blades 150 are arranged with respect to the internal sheath 136 such that the rotation of the internal sheath 136 causes a rotation of the blades 150. In an embodiment, tips 152 of the blades 150 are located distal to the second end 114 of the handpiece portion 110. In the present disclosure, "the tips 152 of the blades 150" are alternatively referred as the "tips 152 of the morcellator device 100". The tips 152 of the blades 150 are exposed via the opening 140 during rotation and are configured to morcellate the tissues present at the opening 140 during the surgical procedure. For the purpose, the tips 152 of the blades 150 are substantially sharpened to ease the morcellation of the tissues. The internal sheath 136 is coupled to the motor 802 and hence rotates based on operation of the motor 802.

Specifically, when the morcellator device 100 is used for performing a surgical procedure, the first end 132 of the rod 130 is located inside the subject's body with the tips 152 of the blades 150 being in contact with the tissue to be morcellated (as exposed via the opening 140). When the motor 802 is switched ON, the internal sheath 136 rotates causing rotation of the blades 150, thereby morcellating the tissue in contact therewith. Further, the suction source 122 is configured to suction the morcellated tissue pieces via the rod 130 and extract the same out of the morcellation device 100. In an embodiment, the morcellated tissues may be transported via the radial gap defined between the internal sheath 136 and the external sheath 138. In some embodiments, a separate channel may be provided to extract the morcellated tissues out of the subject's body.

Further, the second end 174 of each wire 170 emerging out of the opening 164 is connected to one grasping nail 180, as illustrated in FIG. 5. The grasping nails 180 are embodied as flexible wires. Preferably, the grasping nails 180 are made of a suitable shape-memory alloy, such as Nitinol, which also exhibits super elasticity. The grasping nails 180 provide flaring ends configured to hold tissues which need to be morcellated. In an embodiment, the morcellator device 100 may include more than two grasping nails 180, such as a "scorpion-tail shape", to aid trapping of the tissues therebetween. In some aspects, the grasping nails 180 may also aid in distancing the surrounding tissues from a region of interest, thereby easing insertion of the rod 130 towards the region of interest. In the illustrated embodiment, the blade 150 are positioned adjacent to the grasping nails 180. Particularly, the blade 150 and the grasping nails 180 lie in a same plane.

Figure 6A:
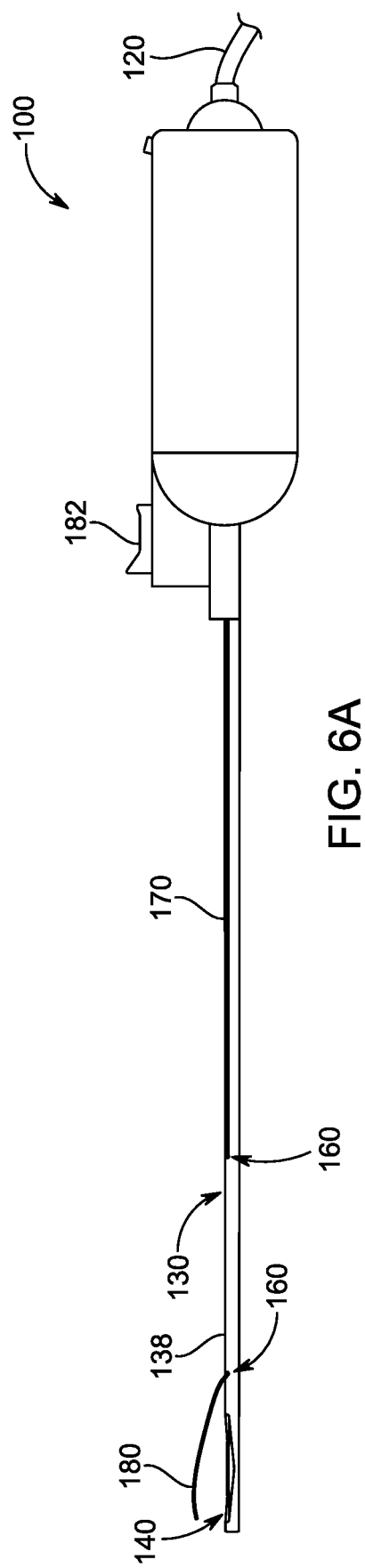
FIG. 6A is a side view of the prostate grasping morcellator device of FIG. 1 with the control button in the first position thereof to have one or more retractable grasping nails in an extended configuration, according to certain embodiments.
Figure 6B:
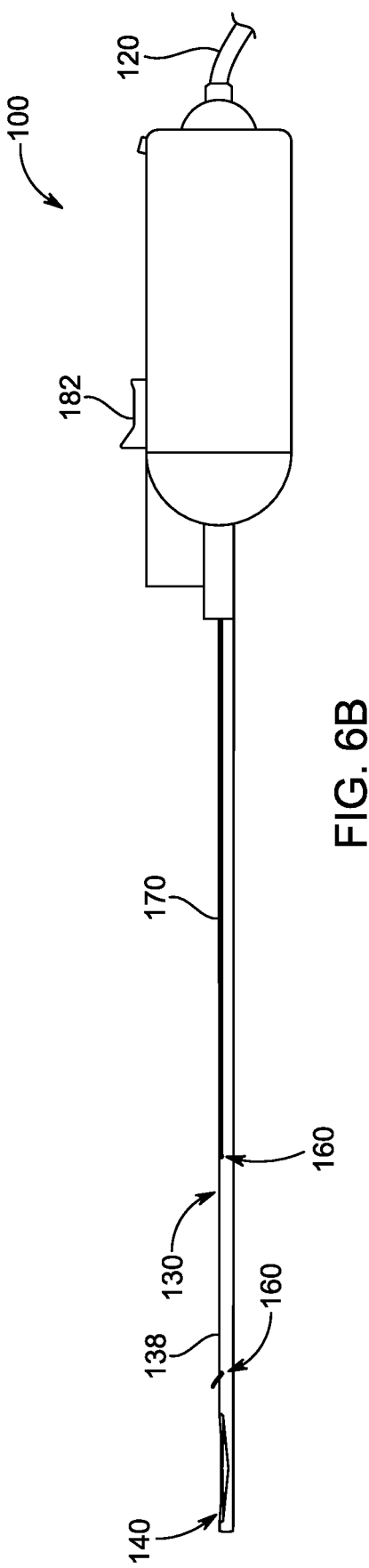
FIG. 6B is a side view of the prostate grasping morcellator device of FIG. 1 with the control button in the second position thereof to have the one or more retractable grasping nails in a retracted configuration, according to certain embodiments.

Referring to FIG. 6A and FIG. 6B, side views of the morcellator device 100 with two different operational positions of the control button 182 are illustrated, according to an embodiment of the present disclosure. FIG. 6A illustrates a default position of the morcellator device 100. In such default position, the control button 182 is located proximal to the second end 114 of the handpiece portion 110. As such, no tension is applied on the wires 170. Additionally, the grasping nails 180 remain in a flared condition at the first end 132 of the rod 130. In operation, when the control button 182 is slid along the groove 184 and moved away from the second end 114 of the handpiece portion 110, the wires 170 are pulled in a direction of the movement of the control button 182. Consequently, the grasping nails 180 are pulled into the tunnel 160 as shown in FIG. 6B. Movement of the control button 182 back to the default position causes the grasping nails 180 to emerge out of the tunnels 160 and regain a shape corresponding to the flared condition, by virtue of the characteristic of the shape-memory alloy. Therefore, the control button 182 is configured to control movement, such as retraction and extension, of the grasping nails 180. Such movement of the grasping nails 180 may hold the tissues to be morcellated or distance other tissues from the tissues to be morcellated, until the opening 140 defined in the rod 130 is in contact with the tissue of interest inside the subject's body to perform morcellation with aid of the blades 150.

Figure 7:
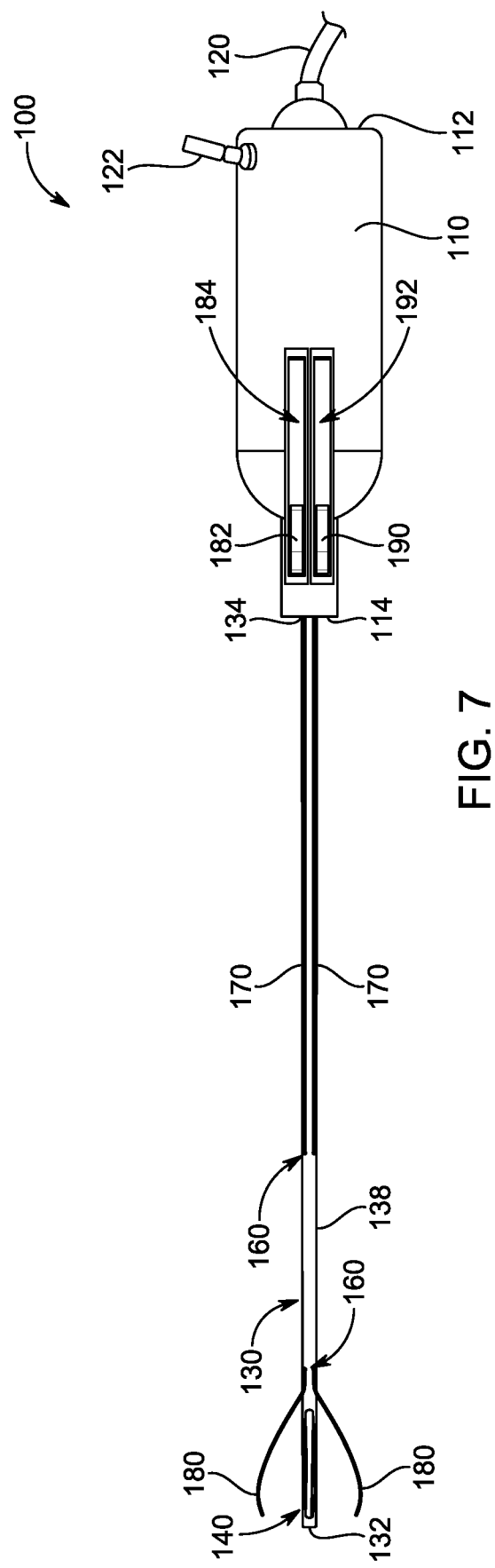
FIG. 7 is a top view of a prostate grasping morcellator device having a second button, according to certain embodiments.

FIG. 7 illustrates the morcellator device 100, according to another embodiment of the present disclosure. The morcellator device 100 may include a second control button 190 in addition to the first control button 182. The second control button 190 is mounted adjacent to the first control button 182. Further, a second groove 192 is defined adjacent the first groove 184 and extends along the longitudinal axis "A" in the handpiece portion 110 and is configured to movably receive the second control button 190. The second control button 190 is positioned such that the user can conveniently access, while also being able to access the first control button 182. In some embodiments, the second groove 192 may be formed at a location diametrically opposite with respect to the first groove 184 in the handpiece portion 110 or at any other suitable location of the circumferential wall of the handpiece portion 110. Preferably, the second control button 190 is coupled to the internal sheath 136. In operation, when the second control button 190 is moved towards the first end 112 of the handpiece portion 110, the internal sheath 136 may be pulled, thereby increasing a size of the opening 140 defined in the rod 130. On the other hand, when the second control button 190 is moved away from the first end 112 of the handpiece portion 110 inside the second groove 192, the internal sheath 136 is pushed towards the first end 132 of the rod 130, thereby decreasing the size of the opening 140 in the rod 130. Thus, the second button 190 may be used to control the size of the opening 140 in the rod 130 as desired. Such variation to the size of the opening 140 may allow less quantity of tissues to be made available for morcellation and suction. In some embodiments, suction power may be set based on the size of the opening 140 or the position of the second control button 190. For example, the suction power may be increased when the size of the opening 140 decreased, and vice versa.

Figure 8:
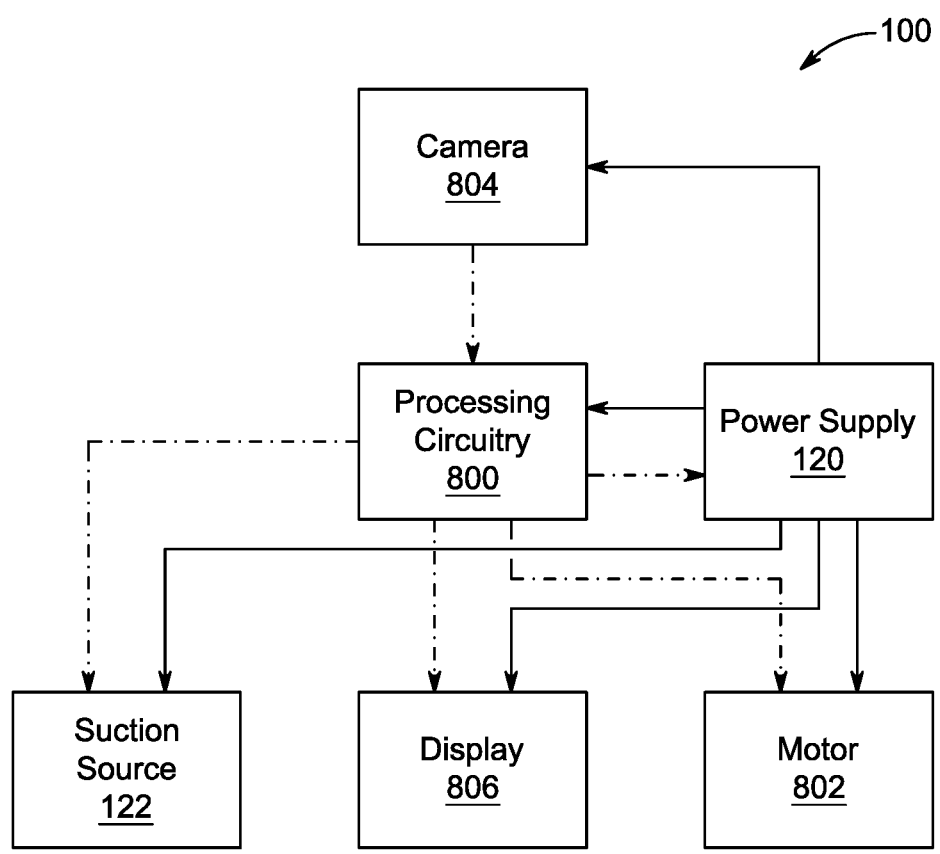
FIG. 8 is an exemplary block diagram of a circuit for the prostate grasping morcellator device of FIG. 1, according to certain embodiments.

Referring now to FIG. 8, an exemplary block diagram of a circuit for the morcellator device 100 is illustrated, showing connections between various components. The illustrated circuit (also represented by the reference numeral 100) utilizes solid lines to represent connections for transferring electrical power and dotted-dashed lines to represent connections for transferring communication signals. As shown, the morcellator device 100 includes a processing circuitry 800 (embodied as a controller 1000 in FIG. 10). The processing circuitry 800 may be powered by the power supply 120. In an aspect, the processing circuitry 800 may be located within the handpiece portion 110 and may be embodied as a processing device, system, or part thereof that controls at least one operation of the morcellator device 100. In some examples, the processing circuitry 800 may be implemented as hardware, firmware or software, or combination thereof. It should be noted that the functionality associated with any particular controller may be centralized or distributed, whether locally or remotely. Such hardware may be a multi-core processor, a single core processor, or a combination of one or more multi-core processors and one or more single core processors. For example, the one or more processors may be embodied as one or more of various processing devices, such as a coprocessor, a microprocessor, a controller, a digital signal processor (DSP), a processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, or the like, implementing a memory. Further, the memory may include one or more non-transitory computer-readable storage media that can be read or accessed by other components in the device. The memory may be any computer-readable storage media, including volatile and/or non-volatile storage components, such as optical, magnetic, organic, or other memory or disc storage, which can be integrated in whole or in part with the device. In some examples, the memory may be implemented using a single physical device (e.g., optical, magnetic, organic, or other memory or disc storage unit), while in other examples, the memory may be implemented using two or more physical devices without any limitations.

The processing circuitry 800 is configured to control operations of the morcellator device 100 by primarily controlling the motor 802. As shown, the processing circuitry 800 may be disposed in communication with the motor 802. The processing circuitry 800 may transmit independent control signals to the motor 802 for regulating (switch ON and OFF) rotation of the motor 802, and thus the internal sheath 136, thereby rotating the blades 150. Additionally, the processing circuitry 800 may control the power supply 120 to independently regulate electrical power supply to the motor 802, and thereby control the rotational speed of the output shaft of the motor 802, and thus the rotational speed of the blades 150. Such arrangement may be contemplated by a person skilled in the art and thus has not been described further for the brevity of the present disclosure.

Further, the processing circuitry 800 may control operations of the suction source 122 in the morcellator device 100. As shown, the processing circuitry 800 may be disposed in communication with the suction source 122. The processing circuitry 800 may transmit independent control signals to the suction source 122 for regulating (switch ON and OFF) the suction source 122 and may further control the power supply 120 to independently regulate electrical power supply to the suction source 122, thereby controlling suction power and suction rate of the morcellated tissues through the morcellator device 100. Again, such arrangement may be contemplated by a person skilled in the art and thus has not been described further for the brevity of the present disclosure.

In an aspect of the present disclosure, the morcellator device 100 further includes a camera 804. The term "camera", as used herein, covers any kind of structure for capturing an image or a series of images, e.g., for making a video sequence. The camera 804 may be in the form of a pinhole camera or an endoscope, as known in the art. The camera 804 may be disposed in communication with the processing circuitry 800, which may provide functionality of CCD, CMOS chip, etc., as required for processing captured images. In the morcellator device 100, the camera 804 may be constituted by a lens located in an annular aperture at the first end 132 of the rod 130. The morcellator device 100 may include fiber optical cables or other cables, extending from the lens of the camera 804 through the rod 130 (specifically defined radial gap between the internal sheath 136 and the external sheath 138 therein) to the processing circuitry 800. The camera 604 may capture images of an environment surrounding tips of the morcellator device 100. As shown, the camera 804 may be powered by the power supply 120. Further, the morcellator device 100 may include a display 806 configured to display the captured images by the camera 804. For this purpose, the display 806 may be connected to the processing circuitry 800 to receive the processed images to be rendered thereby. As used herein, the term "display" refers to any device configured to display the captured images or video and may either be embedded on the handpiece portion 110 or may be embodied as an independent device located distant from the morcellator device 100.

In an aspect of the present disclosure, the processing circuitry 800 may control extension and retraction of the grasping nails 180. For this purpose, the morcellator device 100 may include an actuator (not shown), such as a linear actuator as known in the art, associated with the first control button 182 to cause movement (sliding) thereof, and thereby control the extension and retraction of the grasping nails 180. Further, in an aspect of the present disclosure, the processing circuitry 800 may control the size of the opening 140. For this purpose, the morcellator device 100 may include another actuator (not shown), such as a linear actuator as known in the art, associated with the second control button 190 to cause movement (sliding) thereof, and thereby control the movement of the internal sheath 136 and thus expansion and contraction of the size of the opening 140.

Figure 9:
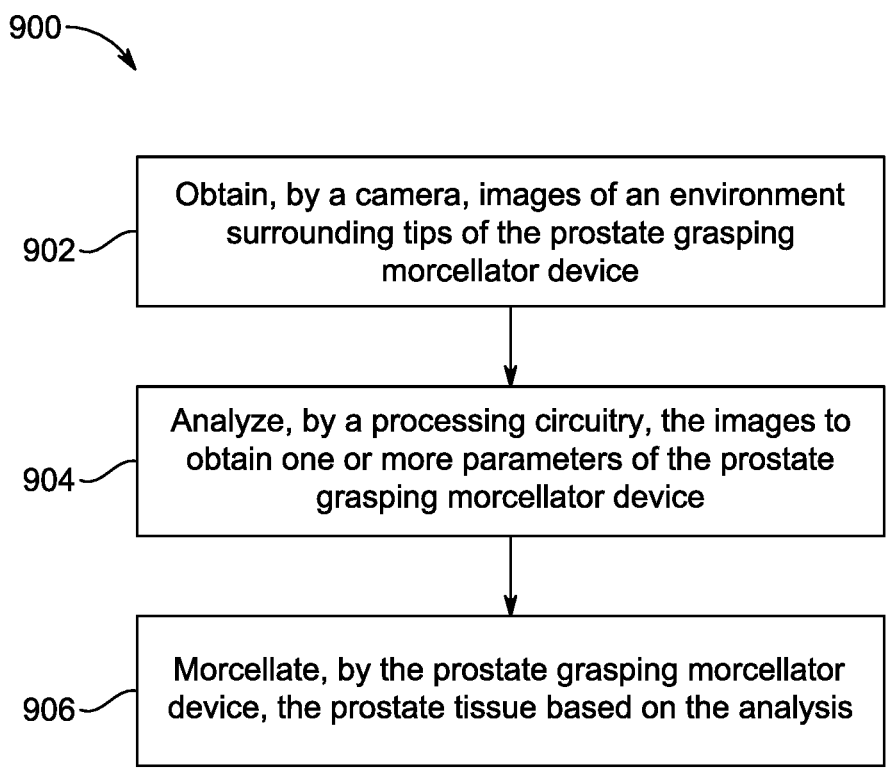
FIG. 9 is an exemplary flowchart of a method of morcellating prostate tissue with a prostate grasping morcellator device, according to certain embodiments.

Referring to FIG. 9, an exemplary flowchart of a method 900 of morcellating prostate tissue with the morcellator device 100 is illustrated. The method 900 is described in conjunction with FIG. 1 through FIG. 8.

At step 902, the method 900 includes obtaining, by the camera 804, images of an environment surrounding the tips 152 of the prostate grasping morcellator device 100. The camera 804 may be switched ON, manually, or automatically by the processing circuitry 800, to capture image of inside of the subject's body when the first end 132 of the rod 130 of the morcellator device 100 is inserted therein. The captured images of the environment surrounding the tips 152 of the prostate grasping morcellator device 100 may then be rendered on the display 806 by the processing circuitry 800. Such rendered images may help the user (usually, a surgeon) of the morcellator device 100 to locate the tissues of interest, which needs to be morcellated, inside the subject's body, and may then accordingly control position and/or orientation of the morcellator device 100 to cause the tips 152 of the blades 150 to be disposed in contact with the tissues of interest.

At step 904, the method 900 includes analyzing, by the processing circuitry 900, the images to obtain one or more parameters of the prostate grasping morcellator device 100. For example, first the images may be analyzed to determine tissue type, tissue structure, tissue thickness, tissue size, tissue orientation and so on. It may be appreciated that known image processing and machine learning techniques may be applied for this purpose. Further, such determined details may be utilized by the processing circuitry 900 to determine parameters like suitable rotation speed for the blades 150, suitable suction power for the suction source 122, suitable size of the opening 140, and the like. In some examples, the processing circuitry 900 may further provide information about suitable cutting angle, suitable cutting time, and the like based on the analysis. Again, it may be appreciated that known artificial intelligence based techniques may be implemented for the said purpose which may be contemplated by a person skilled in the art and thus not explained herein.

At step 906, the method 900 includes morcellating, by the morcellator device 100, the prostate tissue based on the analysis. The step of morcellating may involve setting the determined parameters for corresponding components of the morcellator device 100 for performing the morcellation process. For example, the motor 802 may be set to rotate corresponding to the determined suitable rotation speed of the blades 150. Further, the step of morcellating may involve using the information provided by the processing circuitry 900, including information about suitable cutting angle, suitable cutting time, and the like during the morcellation process. Once all the determined parameters are set for the corresponding components, the morcellation process may be performed. Since configuration, structure, and components of the morcellator device 100 are described with reference to FIG. 1 to FIG. 8, the same is not repeated here for the purpose of brevity of the description.

The first embodiment of the present disclosure is illustrated with respect to FIG. 1 through FIG. 8. The first embodiment describes the prostate grasping morcellator device 100. The prostate grasping morcellator device 100, comprising the handpiece portion 110 including the motor 802 connected to the power supply 120 on the first end 112 of the handpiece portion 110, the motor 802 rotating the internal sheath 136 in the external sheath 138; the rod 130 connecting to the second end 114 of the handpiece portion 110; one or more retractable grasping nails 180 connecting to the end 132 of the rod 130, the end 132 being distal to the second end 114 of the handpiece portion 110; the control button 182 configured to control the movement of the one or more retractable grasping nails 180, the control button 182 mounted adjacent to the second end 114 of the handpiece portion 110; one or more blades 150 configured to morcellate tissue, the one or more blades 150 being rotated by the motor 802; and the suction source 122 configured to collect morcellated tissue pieces, the suction source 122 proximate to the first end 112 of the handpiece portion 110.

The control button 182 controls retraction of the one or more retractable grasping nails 180. The control button 182 connects to the pair of wires 170 on the external sheath 138, the pair of wires 170 connecting to the retractable grasping nails 180. The pair of wires 170 are located inside the pair of tunnels 160, the pair of tunnels 160 being in the external sheath 138.

The one or more retractable grasping nails 180 are configured to trap tissue. The one or more blades 150 are adjacent to the one or more retractable grasping nails 180. The tips 152 of the one or more blades 150 are located distal to the second end 114 of the handpiece portion 110. The suction source 122 connects to the opening 140, the opening 140 being distal to the second end 114 of the handpiece portion 110, the opening 140 allowing morcellated tissues to flow through the opening 140.

The second embodiment of the present disclosure is illustrated with respect to FIG. 9. The second embodiment describes the method 900 of morcellating prostate tissue with the prostate grasping morcellator device 100 comprising obtaining, by the camera 804, images of the environment surrounding tips 152 of the prostate grasping morcellator device 100; analyzing, by the processing circuitry 800, the images to obtain one or more parameters of the prostate grasping morcellator device 100; morcellating, by the prostate grasping morcellator device 100, the prostate tissue based on the analysis, wherein the prostate grasping morcellator device 100 comprises: the handpiece portion 110 including the motor 802 connected to the power supply 120 on the first end 112 of the handpiece portion 110, the motor 802 rotating the internal sheath 136 in the external sheath 138; the rod 130 connecting to the second end 114 of the handpiece portion 110; one or more retractable grasping nails 180 connecting to the end 132 of the rod 130, the end 132 being distal to the second end 114 of the handpiece portion 110; the control button 182 configured to control the movement of the one or more retractable grasping nails 180, the control button 182 mounted adjacent to the second end 114 of the handpiece portion 110; one or more blades 150 configured to morcellate the prostate tissue, the one or more blades 150 being rotated by the motor 802; and the suction source 122 configured to collect morcellated prostate tissue pieces, the suction source 122 proximate to the first end 112 of the handpiece portion 110.

The one or more retractable grasping nails 180 are configured to trap tissue. The control button 182 controls retraction of the one or more retractable grasping nails 180. The one or more blades 150 are adjacent to the one or more retractable grasping nails 180. The control button 182 connects to the pair of wires 170 on the external sheath 138, the pair of wires 170 connecting to the retractable grasping nails 180. The pair of wires 170 are located inside the pair of tunnels 160, the pair of tunnels 160 being in the external sheath 138. The tips 152 of the one or more blades 150 are located distal to the second end 114 of the handpiece portion 110. The suction source 122 connects to the opening 140, the opening 140 being distal to the second end 114 of the handpiece portion 110, the opening 140 allowing morcellated prostate tissues to flow through the opening 140.

The third embodiment of the present disclosure is illustrated with respect to FIG. 1 through FIG. 8. The third embodiment describes the prostate grasping morcellator device 100. The prostate grasping morcellator device 100, comprising the handpiece portion 110 including the motor 802 and the control button 182; the rod 130 connecting to the second end 114 of the handpiece portion 110; the plurality of retractable grasping nails 180 connecting to the end 132 of the rod 130; the plurality of blades 150 connected to the motor 802, the plurality of the blades 150 being connected to the rod 130; the suction source 122 in fluid communication with the end 132 of the rod 130 adjacent to the plurality of blades 150.

The motor 802 rotates the internal sheath 136 in the external sheath 138. The end of the rod 130 is distal to the handpiece portion 110. The plurality of blades 150 is used to morcellate the prostate tissues.

Figure 10:
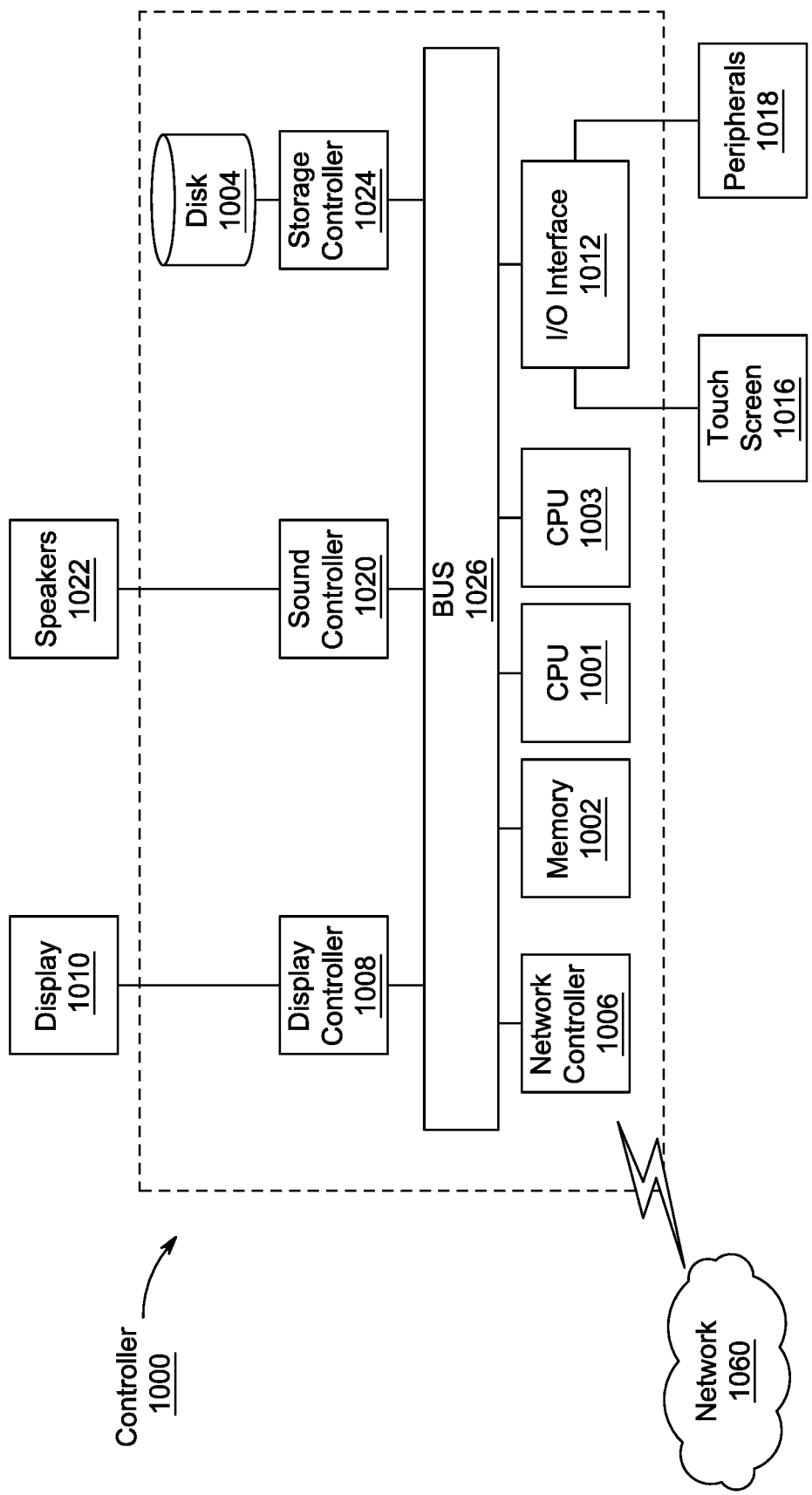
FIG. 10 is an illustration of a non-limiting example of details of computing hardware used in the computing system, according to certain embodiments.

Next, details of the hardware description of the processing circuitry 800 of FIG. 8 according to exemplary embodiments is described with reference to FIG. 10. In FIG. 10, the controller 1000 described is representative of the processing circuitry 800 of FIG. 8 in which the controller 1000 is a computing device which includes a CPU 1001 which performs the processes described above/below. The process data and instructions may be stored in memory 1002. These processes and instructions may also be stored on a storage medium disk 1004, such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 1001, 1003 and an operating system such as Microsoft Windows 10, Microsoft Windows 10, UNIX, Solaris, LINUX, Apple MAC-OS and other systems known to those skilled in the art.

The hardware elements in order to achieve the computing device may be realized by various circuitry elements, known to those skilled in the art. For example, CPU 1001 or CPU 1003 may be, but not limited to, a Xenon or Core processor from Intel of America or an Opteron processor from AMD of America, or may be other processor types that would be recognized by one of ordinary skill in the art. Alternatively, the CPU 1001, 1003 may be implemented on an FPGA, ASIC, PLD or using discrete logic circuits, as one of ordinary skill in the art would recognize. Further, CPU 1001, 1003 may be implemented as, but not limited to, multiple processors cooperatively working in parallel to perform the instructions of the inventive processes described above.

The controller 1000 includes a network controller 1006, such as an Intel Ethernet PRO network interface card from Intel Corporation of America, for interfacing with a network 1060. As can be appreciated, the network 1060 can be a public network, such as the Internet, or a private network such as an LAN or WAN network, or any combination thereof and can also include PSTN or ISDN sub-networks. The network 1060 can also be wired, such as an Ethernet network, or can be wireless such as a cellular network including EDGE, 3G and 4G wireless cellular systems. The wireless network can also be WiFi, Bluetooth, or any other wireless form of communication that is known.

The controller 1000 further includes a display controller 1008, such as a NVIDIA GeForce GTX or Quadro graphics adaptor from NVIDIA Corporation of America for interfacing with a display 1010 (shown as display 806 in FIG. 8), such as a Hewlett Packard HPL2445w LCD monitor. A general purpose I/O interface 1012 interfaces with a touch screen panel 1016 on or separate from display 1010. General purpose I/O interface also connects to a variety of peripherals 1018 including printers and scanners, such as an OfficeJet or DeskJet from Hewlett Packard.

A sound controller 1020 is also provided in the computing device such as Sound Blaster X-Fi Titanium from Creative, to interface with speakers/microphone 1022 thereby providing sounds and/or music.

The general purpose storage controller 1024 connects the storage medium disk 1004 with communication bus 1026, which may be an ISA, EISA, VESA, PCI, or similar, for interconnecting all of the components of the computing device. A description of the general features and functionality of the display 1010, as well as the display controller 1008, the storage controller 1024, the network controller 1006, the sound controller 1020, and the general purpose I/O interface 1012 is omitted herein for brevity as these features are known.

The above-described hardware description is a non-limiting example of corresponding structure for performing the functionality described herein.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A prostate grasping morcellator device, comprising:
a handpiece portion including a motor connected to a power supply on a first end thereof, the motor rotating an internal sheath in an external sheath;
a rod connecting to a second end of the handpiece portion;
one or more retractable grasping nails connecting to an active end of the rod, the active end of the rod being distal to the second end of the handpiece portion;
a control button configured to control a movement of the one or more retractable grasping nails, the control button mounted proximal to the second end of the handpiece portion;
one or more blades configured to morcellate tissue, the one or more blades being rotated by the motor; and
a suction source configured to collect morcellated tissue pieces, the suction source proximal to the first end of the handpiece portion,
wherein the control button connects to a pair of wires on or in the external sheath, the pair of wires connecting to the retractable grasping nails.

2. The prostate grasping morcellator device of claim 1, wherein the control button is configured to extend and retract the one or more retractable grasping nails.

3. The prostate grasping morcellator device of claim 1, wherein the pair of wires are located inside a pair of tunnels in the external sheath.

4. The prostate grasping morcellator device of claim 1, wherein the one or more retractable grasping nails are configured to trap tissue.

5. The prostate grasping morcellator device of claim 1, wherein the one or more blades are adjacent to the one or more retractable grasping nails.

6. The prostate grasping morcellator device of claim 1, wherein tips of the one or more blades are located at the active end of the rod.

7. The prostate grasping morcellator device of claim 1, wherein the suction source connects to an opening, the opening being distal to the second end of the handpiece portion, the opening allowing morcellated tissues to flow through the opening.

* * * * *